United States Patent
Hommes et al.

(10) Patent No.: US 10,946,211 B2
(45) Date of Patent: Mar. 16, 2021

(54) NON-MELATONIN SUPPRESSING LIGHT SOURCE WITH A CRI THAT APPROACHES THAT OF WHITE LIGHT

(71) Applicant: SIGNIFY HOLDING B.V., Eindhoven (NL)

(72) Inventors: Vanja Hommes, Assen (NL); Lucas Josef Maria Schlangen, Eindhoven (NL); Marina Cecilia Gimenez, Groningen (NL); Debra Jean Skene, London (GB); Victoria Louise Revell, London (GB)

(73) Assignee: SIGNIFY HOLDING B.V., Eindhoven (NL)

( * ) Notice: Subject to any disclaimer, the term of this patent is extended or adjusted under 35 U.S.C. 154(b) by 663 days.

(21) Appl. No.: 15/028,143

(22) PCT Filed: Oct. 8, 2014

(86) PCT No.: PCT/EP2014/071480
§ 371 (c)(1),
(2) Date: Apr. 8, 2016

(87) PCT Pub. No.: WO2015/052207
PCT Pub. Date: Apr. 16, 2015

(65) Prior Publication Data
US 2016/0243379 A1    Aug. 25, 2016

(30) Foreign Application Priority Data
Oct. 9, 2013  (EP) ..................... 13187843

(51) Int. Cl.
*A61N 5/06*     (2006.01)
*H05B 45/20*    (2020.01)
(Continued)

(52) U.S. Cl.
CPC ........... *A61N 5/0618* (2013.01); *A61M 21/02* (2013.01); *F21K 9/64* (2016.08); *F21S 6/003* (2013.01);
(Continued)

(58) Field of Classification Search
CPC .......... A61M 2021/0044; A61M 21/02; A61N 2005/0636; A61N 2005/0654;
(Continued)

(56) References Cited

U.S. PATENT DOCUMENTS

2008/0266690 A1* 10/2008 Toda .................. A61M 21/02
                                                         359/885
2010/0174345 A1*  7/2010 Ashdown ............ A61N 5/0618
                                                         607/88
(Continued)

FOREIGN PATENT DOCUMENTS

EP       2094064 A1     8/2009
JP    2009059677 A     3/2009
(Continued)

*Primary Examiner* — Niketa I Patel
*Assistant Examiner* — Vynn V Huh
(74) *Attorney, Agent, or Firm* — Meenakshy Chakravorty (57) ABSTRACT

The invention provides a lighting unit configured to generate white light wherein the white light has a spectral intensity in the visible wherein at least 40% of all photons in the wavelength range of 400-500 nm are found in the wavelength range of 430-445 nm (see also FIG. 1b). The lighting unit may especially be used for increasing alertness of a human while not or minimally suppressing melatonin production of the human.

16 Claims, 5 Drawing Sheets

(51) Int. Cl.
*A61M 21/02* (2006.01)
*F21K 9/64* (2016.01)
*F21S 6/00* (2006.01)
*F21V 9/08* (2018.01)
*A61M 21/00* (2006.01)

(52) U.S. Cl.
CPC ............... *F21V 9/08* (2013.01); *H05B 45/20* (2020.01); *A61M 2021/0044* (2013.01); *A61N 2005/0636* (2013.01); *A61N 2005/0654* (2013.01); *A61N 2005/0658* (2013.01); *A61N 2005/0663* (2013.01); *A61N 2005/0667* (2013.01)

(58) Field of Classification Search
CPC .... A61N 2005/0658; A61N 2005/0663; A61N 2005/0667; A61N 5/0618; F21K 9/56; F21S 6/003; F21V 9/08; H05B 33/086
See application file for complete search history.

(56) References Cited

U.S. PATENT DOCUMENTS

| 2011/0025187 A1* | 2/2011 | Tews ................... A61N 5/0618 313/487 |
| 2012/0069551 A1* | 3/2012 | Bues ................. G02F 1/133603 362/97.2 |
| 2016/0023017 A1* | 1/2016 | Moore-Ede .......... A61N 5/0618 607/88 |

FOREIGN PATENT DOCUMENTS

| JP | 2011258649 A | 12/2011 |
| WO | 2002020079 A1 | 3/2002 |
| WO | 2012130958 A1 | 10/2012 |

* cited by examiner

NON-MELATONIN SUPPRESSING LIGHT SOURCE WITH A CRI THAT APPROACHES THAT OF WHITE LIGHT

CROSS-REFERENCE TO PRIOR APPLICATIONS

This application is the U.S. National Phase application under 35 U.S.C. § 371 of International Application No. PCT/EP2014/071480, filed on Oct. 8, 2014, which claims the benefit of European Patent Application No. 13187843.1, filed on Oct. 9, 2013. These applications are hereby incorporated by reference herein.

FIELD OF THE INVENTION

The invention relates to a lighting unit and a lighting system comprising such lighting unit that may especially be used in nocturnal situations.

BACKGROUND OF THE INVENTION

Lighting adapted to specific situations or increasing alertness is known in the art. WO/2002/020079, for instance, describes a method for controlling the alertness of a human subject and a light source for use in this method and use of a light source for this method. The method comprises exposure of a human subject during an exposure period to suitable light radiation without substantially influencing the phase of a melatonin cycle. Melatonin is a sleep-hormone that can be used to control the alertness of a human subject. WO/2002/020079 describes that the suitable light radiation is specified by an output fraction of melatonin suppressive radiation (Melatonin Watt/Watt) and light output (lumen/Watt), the output fraction and light output being adjusted to obtain the desired effect on the phase of said cycle.

US2011/0025187 describes a low-pressure gas-discharge lamp which, with its light in the red spectral region, influences the biological circadian rhythm by controlling melatonin secretion. Amongst others, a blue-absorbent phosphor is applied to absorb the mercury emission line at 405 nm and especially at 436 nm.

SUMMARY OF THE INVENTION

Light powerfully regulates the so-called non-visual responses. These responses include what is known as circadian responses (e.g. 24 h rhythms in physiology and behavior) as well as the acute effects of light (e.g. increase alertness and melatonin suppression). However, enhancing non-visual responses is not always desirable. An example may be the one of night (shift) workers. Being exposed to light at night on regular basis has a negative impact on human health. This is considered to be partially due circadian misalignment, and also the suppression of the melatonin hormone may play a role. On the other hand, light at night is known to increase alertness something desirable while working. In order to overcome this dilemma blue depleted fluorescent light sources (unpublished data) or blue light blocker goggles have been suggested. Goggles blocking all wavelengths below 540 nm, or below 530 nm were shown to lead to melatonin levels similar to those observed under dim light condition (i.e. relatively no suppression of melatonin was observed).

In circumstances when light exposure is needed for visual tasks but when it is not desired to suppress melatonin production and influence the biological clock one needs to use light sources that are depleted in blue light (400-530 nm). Such light conditions are suboptimal for the visual task execution (lower color rendering index), and have less alerting properties (of interest for night shift execution) than full spectrum light conditions.

At present, solutions developed so far for preventing melatonin suppression while allowing for sufficient alertness are blue light blocking goggles, or alternatively blue depleted light sources. The use of goggles is somehow intrusive, it demands subject's willing to wear them and might not always be comfortable or feasible depending on the tasks to be done. Moreover, blocking out all short wavelengths has the disadvantage of resulting in a poor Color Rendering Index (CRI). Color Rendering Index is a quantitative measure of the ability of a light source to reproduce the colors of various objects faithfully in comparison with an ideal or natural light source. Typical indoor luminaries have the CRI>80. Blue depleted fluorescent light sources for instance could lead to a CRI of about 65, and blue depleted white LED sources have the CRI of 30-50. This results in a not very pleasant atmosphere and furthermore, it can represent a problem in color-critical duties.

Hence, it is an aspect of the invention to provide an alternative lighting unit which preferably further at least partly obviates one or more of above-described drawbacks and/or has the above indicated desired properties.

It has surprisingly been found that when selecting a specific wavelength range within the blue part of the spectrum alertness may be increased while melatonin suppression may be reduced or even be prevented. This wavelength range is especially around about ~435-440 nm. Choosing however wavelengths lower or higher, melatonin suppression may disadvantageously increase. Further, at other wavelengths the (relative) increase is lower whereas in this wavelength region this increase is surprisingly higher.

This invention improves on both above aspects by adding violet light (≈435-440 nm) to the spectrum, which was found to have stronger alerting properties than blue light (especially in a low intensity range suitable for night illumination), whereas still not significantly suppressing melatonin. Further, the CRI may increase substantially when compared to prior art solutions where a substantial part of the blue-green region is blocked. This may increase safety.

Hence, in a first aspect the invention provides a lighting unit configured to generate white light wherein the white light has a spectral intensity in the visible wherein especially at least 40%, especially at least 50%, even more especially at least 55%, such as at least 60%, of all photons in the wavelength range of 400-500 nm are found in the wavelength range of 400-445 nm, especially in the wavelength range of 430-445 nm. Such lighting unit may provide light that is (substantially) white to the eye, may increase alertness, but may nevertheless reduce or even prevent melatonin suppression. The light generated by the lighting unit is herein also indicated as "lighting unit light". The term "in the visible" may also be indicated as "in the visible range" or "in the visible wavelength range".

Hence, especially such lighting unit may amongst others be used for increasing alertness of an animal, especially a vertebrate, even more especially a human. Alternatively or additionally, such lighting unit may amongst others be used for providing (white) light while not or minimally suppressing melatonin production of such animal, especially such vertebrate, even more especially said human. Further, especially the lighting unit may be used during a period selected from 6 pm to 9 am. For example, the lighting unit may (be configured to) provide light during the period of 9 pm to 6 am. For instance, the lighting unit (or lighting system, see also below), may include a sensor configured to sense time or light intensity of general lighting (including natural sources of light), and switch to the light as defined herein, i.e. especially white light having a spectral intensity in the visible wherein at least 40% of all photons in the wavelength range of 400-500 nm are found in the wavelength range of 400-445 nm, especially in the wavelength range of 430-445 nm. Such lighting unit (or lighting system, see also below) may for instance advantageously be used for illuminating a space, such as a work space.

Hence, the invention, especially the lighting unit, may in one aspect be used to control sleepiness (of an animal, especially a vertebrate, even more especially a human) and/or yet in another aspect the invention, especially the lighting unit, may be used to control alertness (of an animal, especially a vertebrate, even more especially a human). Here, the term "control" may also refer to influence.

The space, such as indicated above, may for instance be (part of) a hospitality area, such as a restaurant, a hotel, a clinic, or a hospital, etc. The term "space" may also relate to (a part of) an office, a department store, a warehouse, a cinema, a church, a theatre, a library, etc. However, the term "space" may also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a (night shift) control room, a security room, etc. As indicated above, the color of the light may be white or at least close to (perfect) white light. Hence, a good color rendering may be obtained, while being able to control a biological response, such as alertness and melatonin production. The lighting unit may be used to prevent the disadvantageous melatonin suppressing effect of normal light.

Especially the lighting unit may be used for providing light with a CRI (color rendering index) above 60, more especially above 65, even more especially above 70, such as at least 75. Especially, the lighting unit may be used for providing such light, while not or minimally suppressing melatonin production of the human (or (another) vertebrate). Hence, the invention may also provide a lighting method that enables for high photopic luxes, a high CRI and minimal or modest melatonin suppression, especially by a reduced level of photons in the band between 440 and 490 nm, even more especially in the band between 440-540 nm, such as 460-490 nm.

Hence, the invention also provides in a further aspect a method of providing light in a space comprising providing light with the lighting unit as defined herein to said space. For instance, the method may include providing said light with total melanopic illuminance in the range of 90-1500, especially 90-1000, even more especially 90-200 mlux. The melanopic illuminance is e.g. defined in Enezi, J. A., Revell, V., Brown, T., Wynne, J., Schlangen, L., & Lucas, R. A "Melanopic" Spectral Efficiency Function Predicts the Sensitivity of Melanopsin Photoreceptors to Polychromatic Lights. Journal of Biological Rhythms, 26(4), 314-323, which is incorporated herein by reference (see especially formula 3 in this paper). In a further specific embodiment, the lighting unit is configured to provide lighting unit light having a ratio of the total melanopic illuminance (in mlux) to the total irradiance (in lux) of at least 1:100, such as at least 1.5:100, like at least 2:100. In the present invention, it seems that advantageous results may be obtained by circumventing triggering the opsin:vitamin A based photopigment, such as defined in above indicated paper.

The lighting unit described herein can be any lighting unit with one or more light sources. The lighting unit may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, green house lighting systems, horticulture lighting, or LCD backlighting.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL.

The terms "violet light" or "violet emission" especially relates to light having a wavelength in the range of about 380-440 nm. The terms "blue light" or "blue emission" especially relates to light having a wavelength in the range of about 440-490 nm (including some violet and cyan hues). The terms "green light" or "green emission" especially relate to light having a wavelength in the range of about 490-560 nm. The terms "yellow light" or "yellow emission" especially relate to light having a wavelength in the range of about 540-570 nm. The terms "orange light" or "orange emission" especially relate to light having a wavelength in the range of about 570-600. The terms "red light" or "red emission" especially relate to light having a wavelength in the range of about 600-750 nm. The term "pink light" or "pink emission" refers to light having a blue and a red component. The terms "visible", "visible light" or "visible emission" refer to light having a wavelength in the range of about 380-750 nm.

The lighting unit may comprise one or more light sources. The light source is configured to generate light. The light from the light source is herein also indicated as light source light. The term "light source" may also refer to a plurality of light sources. Likewise, the term "lighting unit" may also refer to a plurality of lighting units. In a specific embodiment, the light source comprises a solid state LED light source (such as a LED or laser diode). The term "light source" may also relate to a plurality of light sources, such as 2-20 (solid state) LED light sources. Hence, the term LED may also refer to a plurality of LEDs. However, the lighting unit may also comprise in addition or alternatively other types of light sources. Below, a non-limiting number of configurations are further elucidated.

Before some of these configurations are discussed, first some further aspects of the lighting unit in general are discussed.

As indicated above, the lighting unit is especially configured to generate white light wherein the white light has a spectral intensity in the visible wherein especially at least 40%, especially at least 50%, even more especially at least 55%, such as at least 60%, of all photons in the wavelength range of 400-500 nm are found in the wavelength range of 400-445 nm, even more especially in the wavelength range of 430-445 nm. In yet a further aspect, the invention provides a lighting unit especially configured to generate white light wherein the white light has a spectral intensity in the visible with photons in the wavelength range of 430-445 nm and optionally having photons in the wavelength range of 445-490 nm, having a ratio of the total number of photons in the wavelength range of 445-490 nm to the total number of photons wavelength range of 430-445 nm of at maximum 1, such as at maximum 0.75, especially at maximum 0.5, such as at maximum 0.3. For instance, the total number of photons in the range of 430-445 nm may be 2 times the total number of photons in the 445-490 range (i.e. the ratio as defined above would then be 0.5). Hence, in an embodiment the white light has a ratio of the total number of photons in the wavelength range of 445-490 nm to the total number of photons wavelength range of 430-445 nm of at maximum 1, especially at maximum 0.75, especially at maximum 0.5, such as at maximum 0.3, such as even equal to or below 0.25.

In yet a further a further aspect, the invention provides a lighting unit especially configured to generate white light wherein the white light has a spectral intensity in the visible with photons in the wavelength range of 400-445 nm and optionally having photons in the wavelength range of 445-490 nm, having a ratio of the total number of photons in the wavelength range of 445-490 nm to the total number of photons wavelength range of 400-445 nm of at maximum 1, such as at maximum 0.75, especially at maximum 0.5, such as at maximum 0.3. At a ratio of e.g. 0.5, there are twice as much photons in the 400-445 nm wavelength range than in the range of 445-490 nm. However, especially a substantial part of the photons in the wavelength range of 400-445 nm is found in the wavelength range of 430-445 nm, such as at least 40%, even more especially at least 60%, such as at least 80%.

Especially, the lighting unit is configured to provide visible light having spectral intensity in the wavelength ranges 380-490 nm, 490-590 nm, and 590-750 nm. The combination of light in these ranges may provide light that may appear white to the eye. The person skilled in the art can choose the amounts and ratios to provide light with the desired similarity to white light and desired CRI. Hence, the lighting unit is especially configured to provide polychromatic light, especially white polychromatic light.

Hence, in a further aspect the invention provides a lighting unit configured to generate visible light having spectral intensity in the wavelength ranges 380-490 nm, 490-590 nm, and 590-750 nm, wherein the light has a spectral intensity in the visible wherein especially at least 40%, especially at least 50%, such as at least 55%, or even more especially at least 60% of all photons in the wavelength range of 400-500 nm are found in the wavelength range of 400-445 nm, especially in the wavelength range of 430-445 nm. Such lighting unit may provide light that is white to the eye, may increase alertness, but may nevertheless reduce or even prevent melatonin suppression.

Especially, as indicated above, the lighting unit is configured to provide light having a spectral intensity in the visible wherein at least 40%, such as at least 50%, of all photons in the wavelength range of 400-500 nm are found in the wavelength range of 400-445 nm, especially 430-445 nm. By this choice, light may be obtained with the above indicated useful property or properties. The phrase "wherein at least 40% of all photons in the wavelength range of 400-500 nm are found in the wavelength range of 430-445 nm" and similar phrases, especially indicates that from all photons generated by the lighting unit in the range of 400-500 nm 40% or more has a wavelength selected from the range of 430-445 nm.

Alternatively or additionally, it appears that good results in terms of alertness (and non-melatonin suppression may) be obtained with light wherein less than 50%, especially less than 40%, even more especially less than 30%, such as even more especially less than 25%, like less than 20% of all photons in the wavelength range of 400-500 nm are found between 445-490 nm.

Hence, in a further specific embodiment a lighting unit is provided (as defined above), configured to generate (white) light wherein at least 40%, especially at least 50%, even more especially at least 55%, such as at least 60%, of all photons in the wavelength range of 400-500 nm, even more especially in the wavelength range of 400-530 nm, yet even more especially in the wavelength range of 400-540 nm, are found in the wavelength range of 400-445 nm, especially 430-445 nm, and wherein less than 50%, especially less than 40%, even more especially less than 30%, such as even more especially less than 25%, like less than 20%, of all photons in the wavelength range of 400-500 nm, or even more especially of all photons in the wavelength range below 500 nm are found between 445-490 nm. Hence, the lighting unit may be configured to provide light that is depleted in photons in the range of 445-490 nm (i.e. blue photons), and even in the entire wavelength range of 445-540 nm (blue and/or green photons).

Hence, in an embodiment less than 30%, such as less than 20%, even more especially less than 10% of all photons in the visible are found in wavelength range of 445-540 nm. In a further specific embodiment, at least 30%, especially at least 40%, especially at least 50%, such as at least 55%, or even more especially at least 60% of all photons in the wavelength range of 400-530 nm, especially in the wavelength range of 400-540 nm, are found in the wavelength range of 400-445 nm, especially 430-445 nm.

Now turning to some specific configurations, the invention provides in an embodiment a lighting unit comprising (a) a first light source configured to generate first light source light having spectral intensity in the visible, wherein especially at least 50% of the photons in the visible (of said first light source light) are found in the wavelength range of 400-445 nm, especially 430-445 nm, and (b) a second light source configured to generate second light source light having spectral intensity in the visible, wherein at least 50% of all photons in the visible (of said second light source light) are found in the range of at least 500 nm, wherein the lighting unit further optionally comprises an optical filter configured to reduce propagation of second light source light having a wavelength below 500 nm, and wherein the first light source and the second light source with optional optical filter are configured to generate said white light. In such embodiment, the white light (generated by the lighting unit during use thereof) comprises said first light source light and said second light source light. The term "at least 500 nm" and similar terms refer to wavelengths of 500 nm and longer wavelengths, such as for instance 550 nm, or 600 nm, etc.

The first light source may for instance be a solid state light source, such as a LED or OLED. However, the first light source may also be a light source that uses an organic or inorganic material to provide the desired luminescence. Such luminescent material may e.g. be excited by a LED and/or by a mercury discharge lamp. The first light source may essentially provide the desired violet-like light mainly in the range of 430-445 nm. The second light source may be any light source that provides light in one or more of the green, yellow, orange, and red. Optionally, such light source may also provide light in the blue. However, the optical filter is especially configured to reduce propagation of (second light source) light below 500 nm.

Especially, the second light source may be configured to provide yellow light, optionally together with red light. In yet another embodiment, the second light source may be configured to provide green light and red light, and optionally yellow light. As indicated above, green components in the light may partly be reduced by the optical filter.

The second light source may for instance be a solid state light source, such as a LED or OLED. However, the second light source may also be a light source that uses an organic or inorganic material to provide the desired luminescence. Such luminescent material may e.g. be excited by a LED and/or by a mercury discharge lamp. However, the second light source may also comprise a fluorescent lamp. Hence, in a specific embodiment the first light source comprises a first solid state light source and the second light source comprises a second solid state light source and a luminescent material configured to convert second solid state light source light into luminescent material light, wherein the second solid state light source with the luminescent material is configured to provide said second light source light, and in another specific embodiment the first light source comprises a first solid state light source and the second light source comprises a fluorescent lamp. Note that different types of light sources may be combined. The fluorescent lamp may especially be configured to provide white light. Undesired blue, and optionally green light, may (substantially) be filtered away by the optical filter, and the blue component of the lighting unit light is provided by the first light source.

Several configurations may be chosen by the person skilled in the art. However, and the first light source and the second light source with optical filter are configured to generate said white light. Hence, the first light source together with the second light source with (its) optical filter provide the lighting unit light.

In yet a further embodiment, the lighting unit as described herein comprises a (first) light source configured to generate light source light having spectral intensity in the visible, an optical filter configured downstream of the light source, wherein the (first) light source and the optical filter are configured to provide said white light downstream of said optical filter, and wherein the optical filter is configured to reduce propagation of light source light having a wavelength in the range of 450-500 nm. In the embodiment described above, the optical filter may only have influence on the light of the second light source. In this embodiment, however, the optical filter is configured downstream of the light source and may thus influence all light that escapes from the lighting unit. For instance, in an embodiment the lighting unit comprises a fluorescent lamp, such as a triband fluorescent lamp, with a broad band blue emission (like based on $BaMgAl_{10}O_{17}$:Eu or similar europium doped compounds). By the optical filter, undesired blue light is reduced. In such embodiment, but also for the other herein described embodiments one or more of the following may apply for the lighting unit light:

(a) at least 40%, especially at least 50%, even more especially at least 55%, such as at least 60%, of all photons in the wavelength range of 400-500 nm are found in the wavelength range of (400-445 nm, especially) 430-445 nm;

(b) less than 50%, especially less than 40%, even more especially less than 30%, such as even more especially less than 25%, like less than 20%, of all photons in the wavelength range of 400-500 nm are found between 445-490 nm;

(c) less than 25%, especially less than 15%, even more especially less than 10% of all photons in the visible are found in wavelength range of 445-540 nm;

(d) at least 40%, especially at least 50%, even more especially at least 55%, such as at least 60% of all photons in the wavelength range of 400-530 nm, especially in the wavelength range of 400-540 nm, are found in the wavelength range of (400-445 nm, especially) 430-445 nm; and (e) having a ratio of the total number of photons in the wavelength range of 445-490 nm to the total number of photons wavelength range of (400-445 nm, especially) 430-445 nm of at maximum 1, such as at maximum 0.75, especially at maximum 0.5.

Hence, one or more of the above indicated conditions a-e may apply.

Optical filters known in the art may be applied, which may either be configured to reduce (substantially) all propagation of visible radiation below 500 nm, or which may be configured to reduce (substantially) all propagation of visible radiation in the wavelength range of 445-490 nm, especially in the wavelength range of 445-500 nm, even more especially in the wavelength range of 445-540 nm, or which may be configured to allow propagation of light in the wavelength range of 430-445 nm and reduce (substantially) propagation of all remaining visible light in the wavelength range below 500 nm, especially below 540 nm. The optical filter may especially be configured to (a) have mean transmission in the wavelength range wherein light should be transmitted of at least 70%, especially at least 80%, even more especially at least 90%, and/or (b) have mean transmission in the wavelength range wherein light should not be transmitted of at maximum 30%, especially at maximum 20%, even more especially at maximum 10%. An optical filter may have one or more of above defined functionalities. Further, also a plurality of optical filters may be applied, which may have different optical properties, and which may be arranged in series to provide the desired optical effect.

In a specific embodiment, the optical filter comprises a luminescent material. Such optical filter may be configured to absorb at least part of visible radiation in a wavelength range, such as below 500 nm, or which may especially be configured to absorb at least part of visible radiation in the wavelength range of 445-490 nm, especially in the wavelength range of 445-500 nm, even more especially in the wavelength range of 445-540 nm. The luminescent material converts at least part of the absorbed (visible) radiation in (visible) radiation (emission) having another wavelength, in general a longer wavelength, and herein especially having a wavelength of at least 490 nm, such as in the yellow, orange and/or red. Hence, by applying an optical filter comprising a luminescent material, also propagation of (visible) radiation may be reduced as this radiation may be converted into luminescence having another wavelength, especially having a wavelength larger than 490 nm, even more especially having a wavelength larger than 540 nm. Anyhow, in specific embodiments the ratio of 445-490 nm radiation to the total radiation in the visible will be larger upstream from the optical filter (with luminescent material) than downstream of the optical filter. The ratio of these respective ratios may e.g. ≥1.05, such as ≥1.1, especially ≥1.5, though larger values may also be possible, dependent upon the spectral distribution of the radiation upstream and downstream of the optical filter (with luminescent material).

In yet a further embodiment, the lighting unit as described herein comprises (a) a first (solid state) light source configured to generate first (solid state) light source light having spectral intensity in the visible, wherein at least 50%, especially at least 60%, even more especially at least 70%, such as at least 80% of the photons in the visible are found in the wavelength range of 400-445 nm, especially 430-445 nm; (b) a second (solid state) light source configured to generate second (solid state) light source light having spectral intensity in the visible, wherein at least 50%, especially at least 60%, even more especially at least 70%, such as at least 80% of the photons in the visible are found in the wavelength range of 500-570 nm; and (c) a third (solid state) light source configured to generate third (solid state) light source light having spectral intensity in the visible, wherein at least 50%, especially at least 60%, even more especially at least 70%, such as at least 80% of the photons in the visible are found in the wavelength range of 600-750 nm; wherein the first (solid state) light source, the second (solid state) light source and the third (solid state) light source are configured to generate said white light. In this embodiment, three (or more) (solid state) sources may be applied: a (solid state) source configured to generate (solid state) source light in the blue (i.e. violet), especially in the wavelength range of 400-445 nm, especially 430-445 nm, a (solid state) source configured to generate (solid state) source light in the green and/or yellow, and a (solid state) source configured to generate (solid state) source light in the red. As indicated above, the term "light source", and likewise also the term "(solid state) light source" may refer to a plurality of (different) ((solid state)) light sources. Further, this embodiment does not exclude the presence of other types of light sources. For instance, the lighting unit may comprise a first light source configured to generate said desired blue light, a second light source configured to generate green light, a further (second) light source configured to generate yellow light, and a third light source configured to generate red light. Further, also optionally one or more optical filters may be applied to filter out undesired blue light in the wavelength range of 445-490 nm.

Also in this embodiment, the person skilled in the art may choose different types of light sources to arrive at the desired lighting unit light. Hence, the first (solid state) light source, the second (solid state) light source and the third (solid state) light source are configured to generate said white light. Together, these light sources provide the above described (white) light.

In a specific embodiment, the first light source comprises a solid state light source and/or the second light source comprises a solid state light source. Optional further light source may especially also comprise solid state light sources.

As indicated above, several configurations are possible. Especially, they may all have in common that the light of the lighting unit is depleted in blue-green light in the range of 445-490 nm, more especially in the range of 445-500 nm, even more especially in the range of 445-540 nm. Hence, in a specific embodiment, the lighting unit has an optical power (Watt) in the wavelength range of 445-490 nm which is less than 50%, especially less than 40%, even more especially less than 30%, of the total optical power in the wavelength range below 500 nm. Even more especially, the lighting unit has an optical power (Watt) in the wavelength range of 445-490 nm which is less than 40%, especially less than 30%, even more especially less than 20%, such as less than 10% of the total optical power in the visible.

Herein, phrases like "below 500 nm" especially indicate in the range of below 500 nm, but equal to or higher than 380 nm. The value of 380 nm is considered to be the lowest wavelength that may still be visible to the human eye.

The optical power in the other spectral ranges may be distributed to provide the desired (white) light. The present invention allows the generation of white light without the detrimental effect (in some circumstances) of melatonin suppression (or with a reduced effect), while having sufficient or even good color rendering. Hence, light may be provided that may be more healthier than normal light (when applied during the night) while on the other hand safety may be improved as objects may be well visible, in contrast to prior art solutions where cut-off filters for wavelength in the blue(green) are applied. Hence, in a further embodiment the lighting unit is configured to provide (white polychromatic) light having a CRI of at least 60, such as especially at least 70, like at least 75. Hence, as indicated above the lighting unit may be used for providing light with a CRI (color rendering index) above 60, while not or minimally suppressing melatonin production of the human. The present invention also allows the generation of white light that is depleted in blue-green but may nevertheless increase alertness while also having sufficient or even good color rendering (and thereby increasing safety and convenience).

In yet a further aspect, the invention provides a lighting system, comprising said lighting unit, and optionally further comprising a control unit and/or optionally further comprising a further lighting unit. Such lighting system may be configured to provide different types of light, such as "normal" light with a relative high blue and/or green component, for instance during the day, and specific light, depleted in blue light having a wavelength in the range of 445-490 nm, such as described herein. For instance, this may be achieved by a switchable optical filter and/or by switching between light sources and/or by controlling the intensity of one or more light sources of the lighting unit. Optionally or additionally, the lighting system may comprise a further lighting unit, which latter lighting unit may be configured to provide light with a "normal" contribution of light in the 445-490 nm wavelength region. By switching between lighting units and/or by controlling relative intensities of the lighting units, the desired type of light may be provided. Alternatively or additionally, the lighting system may (also) be configured to provide different types of light at different locations. Especially in such embodiment, the lighting system may comprise a plurality of lighting units. Hence, the invention also provides a lighting system comprising the lighting unit as defined herein and optionally a further lighting unit, wherein the lighting system is configured to provide at the same time or at different times at least two types of light, with a first type of light comprising said white light and a second type of light having a relative higher contribution within the wavelength range of 450-500 nm to the total spectral intensity in the visible than the first type of light. For instance, at the same time two types of light may be provided at different location or in different directions. At different times, different types of light may be provided at the same location or in the same direction (though of course also at different times also different location or directions may be served). Photons and power can be measured as known to the person skilled in the art.

Photons can e.g. be counted with a photo multiplier (PM) and other photon counting detectors. Photomultiplier (tubes) are known in the art. Optical powers can be measured with e.g. an optical spectrum analyzer (such as a spectrometer). Such spectrometer may also include a photomultiplier and may thus also be used to evaluate the number of photons over the visible part of the spectrum or parts thereof.

The terms "upstream" and "downstream" relate to an arrangement of items or features relative to the propagation of the light from a light generating means (here the especially the (first) light source), wherein relative to a first position within a beam of light from the light generating means, a second position in the beam of light closer to the light generating means is "upstream", and a third position within the beam of light further away from the light generating means is "downstream".

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description, such as "first light source" and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Further, a first light source in one embodiments is not necessarily the same first light source in another embodiment. There may be different embodiments of a first light source, etc.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The drawings are not necessarily on scale.

DETAILED DESCRIPTION OF THE EMBODIMENTS

Figure 1A:
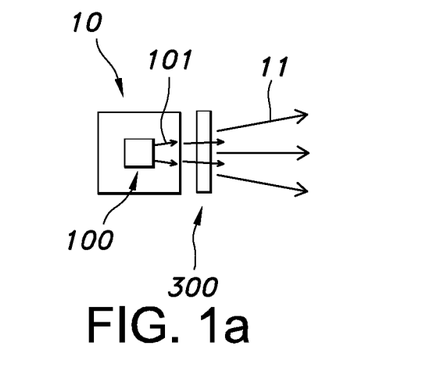
FIGS. 1a-1b schematically depict some aspects of the invention.
Figure 1B:
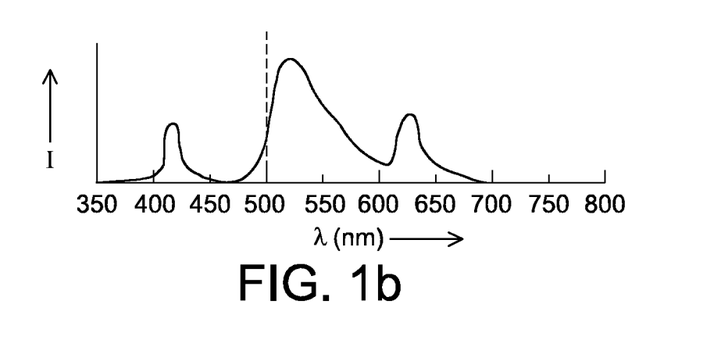

FIG. 1a schematically depicts a lighting unit 10 configured to generate light 11. The light 11 has a spectral intensity in the visible wherein at least 40% of all photons in the wavelength range of 400-500 nm are found in the wavelength range of 430-445 nm. As can be seen in FIG. 1b, there may be a spectral gap between about 500 nm and about 445 nm.

The lighting unit 10 may comprise a light source 100. The term "light source 100" may also refer to a plurality of identical or a plurality of different light sources. The light source 100 generates light 101. The light 101 may be substantially identical to the lighting unit light or light 11. In other words, the light 11 of the lighting unit is substantially based on the light source light 101. However, optionally an optical filter 300 may filter the light source light 101 to provide the desired light 11. For instance, the optical filter 300 may substantially reduce light having a wavelength in the wavelength range of 445-490 nm, even 445-540 nm. FIG. 1b schematically depicts an embodiment wherein at least 40% of all photons in the wavelength range of 400-500 nm are found in the wavelength range of 430-445 nm.

Figure 2A:
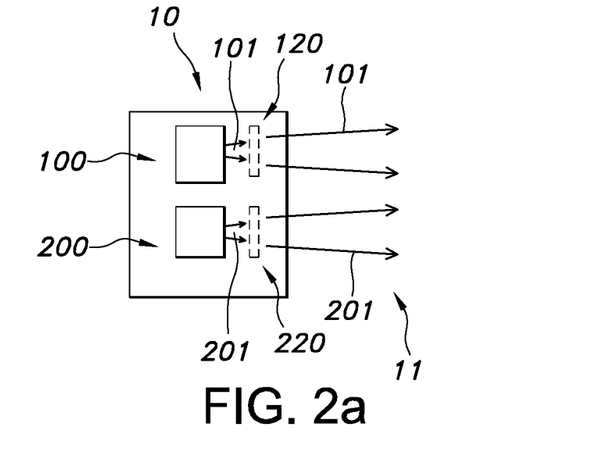
FIGS. 2a-2e schematically depict some further aspects and embodiments of the invention.

FIG. 2a schematically depicts an embodiment of the lighting unit 10 comprising a first light source 100, such as a solid state light source, like a LED and/or OLED, configured to generate first light source light 101 having spectral intensity in the visible, wherein at least 50% of the photons in the visible are found in the wavelength range of especially 430-445 nm. This light source light 101 may escape from the lighting unit 10 substantially unhindered and may thereby be a (important) component of the lighting unit light 10. Further, the lighting unit 10 comprises a second light source 200 configured to generate second light source light 201 having spectral intensity in the visible, wherein at least 50% of all photons in the visible are found in the range of at least 500 nm, wherein the lighting unit 10 further optionally comprises an optical filter 220 configured to reduce propagation of second light source light 201 having a wavelength below 500 nm. The second light source light 201 may thus leave the lighting unit 10 as light depleted in light having a wavelength below 500 nm. For instance, the second light source may be a white fluorescent lamp, of which substantially all light having a wavelength below 500 nm is filtered away by optical filter 220. In this embodiment, in contrast to the above-mentioned variant, not all light source light is filtered, but only light source light of a subset of light sources. The first light source light 101 and the second light source light 201 downstream of the optical filter 220 provide said lighting unit light 11. Hence, the first light source 100 and the second light source 200 with optical filter 220 are configured to generate said (white) light 11. Optionally, also a further optional filter 120 may be included in the first light source. Such optional optical filter may for instance include a luminescent material. Optionally, this may also apply to the optical filter 220. Hence, in a specific embodiment the first light source and the second light source might be identical, but the optical filters provide the different types of light, which in combination provide lighting unit light 11 having the herein described optical properties.

Figure 2B:
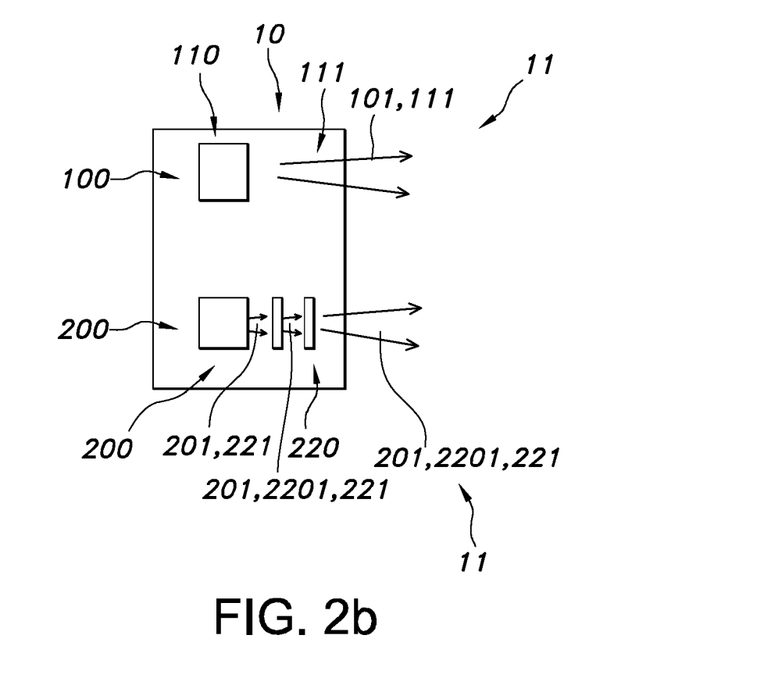

FIG. 2b schematically may depict a variant on FIG. 2a. Here, the first light source 100 may comprises a first solid state light source 110. This first solid state light source 110 is especially configured to provide first solid state light source light 111, which may essentially be in the wavelength range of especially 430-445 nm. The second light source 200 may comprise a second solid state light source 220 and a luminescent material 2200 configured to convert second solid state light source light 221 into luminescent material light 2201. The second solid state light source 220 (together) with the luminescent material 2200 is configured to provide said second light source light 201. Dependent upon the type of second light source 200, the optical filter 200 may be necessary or not. For instance, second solid state light source 220 may be configured to generate UV light and the luminescent material 2200 may be configured to convert this UV solid state light source light 221 into visible light with photons having wavelengths above 490 nm, or even above 530 nm and/or with photons substantially absent in the wavelength range of 445-490 nm, even more especially substantially absent in the wavelength range of 445-540 nm. Also in this embodiment, the first light source 100 and the second light source 200 with optical filter 220 are configured to generate said (white) light 11. Hence, the light 11 may comprise as components the first solid state light source light, the luminescent material light 2201, and optionally remaining second solid state source light 221 (e.g. blue light having a wavelength in the range of 380-445 nm, especially in the range of 430-445 nm).

Figure 2C:
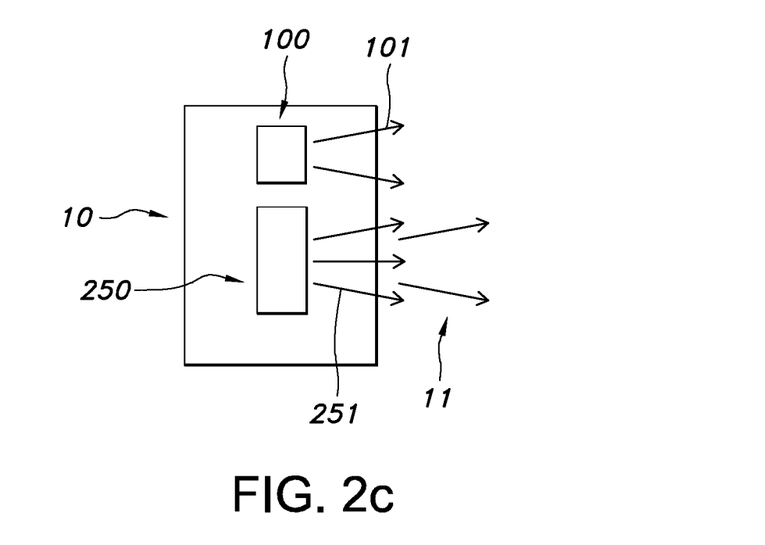

FIG. 2c schematically depicts another variant, wherein the lighting unit 10 comprises a first solid state light source 110 (as first light source 100) and a second light source, wherein the second light source 200 comprises a fluorescent lamp 250. In general, an optical filter may be necessary to deplete the fluorescent lamp light, indicated with reference 251, from light in the 445-490 nm wavelength region. Here, the optical filter is not indicated.

Figure 2D:
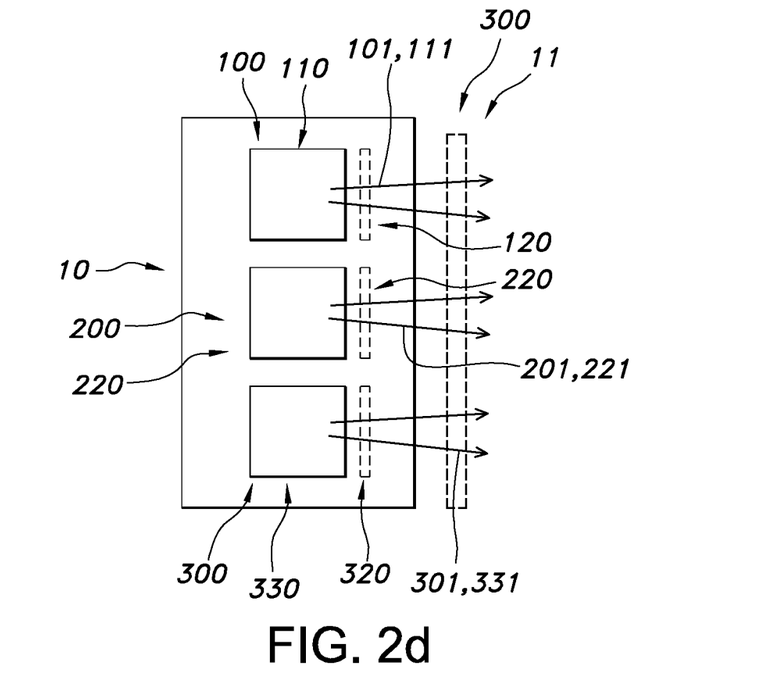

FIG. 2d schematically depicts another variant, wherein the lighting unit 10 comprises a first solid state light source 110, a second solid state light source 220, and a third solid state light source 330. The first solid state light source 110, the second solid state light source 220 and the third solid state light source 330 are configured to generate said white light 11. The first solid state light source 110 may be configured to generate first solid state light source light 111 having spectral intensity in the visible, wherein at least 50% of the photons in the visible are found in the wavelength range of 430-445 nm, i.e. blue(ish) light. Further, the second solid state light source 220 may be configured to generate second solid state light source light 221 having spectral intensity in the visible, wherein at least 50% of the photons in the visible are found in the wavelength range of 500-570 nm, i.e. green and/or yellow light. The third solid state light source 330 may be configured to generate third solid state light source light 331 having spectral intensity in the visible, wherein at least 50% of the photons in the visible are found in the wavelength range of 600-750 nm, i.e. orange and/or red and/or deep red light. By way of example, each light source may independently include an optical filter. The optical filter(s) may be part of the respective light source(s).

Figure 2E:
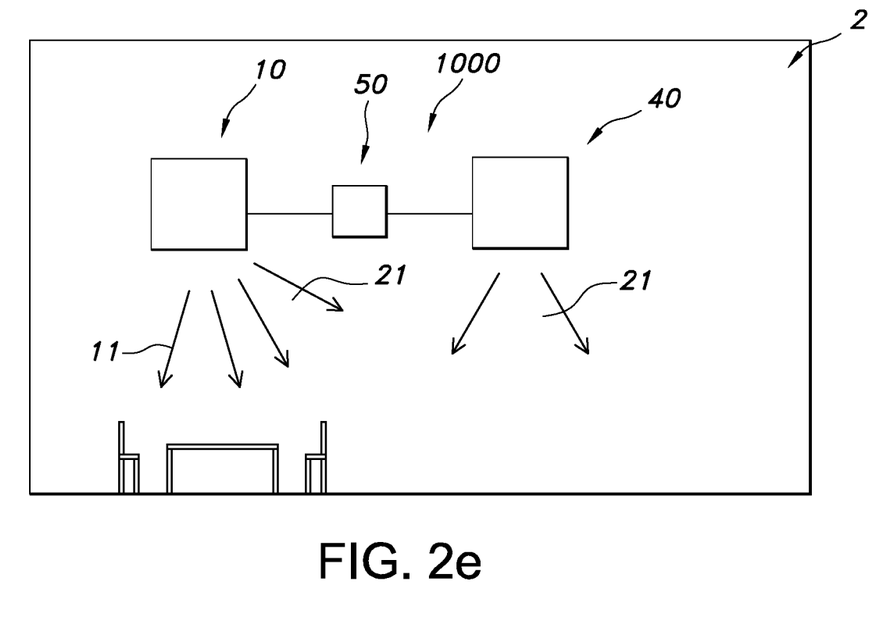

FIG. 2e schematically depicts a lighting system 1000 as well as a space 2, such as a work space, being illuminated with light of said lighting system 100. Here, the lighting system 1000 comprises the lighting unit 10 as defined herein and optionally a further lighting unit 40. This further lighting unit 40 may especially provide another type of light. Hence, the lighting system 1000 may be configured to provide at the same time or at different times at least two types of light, with a first type of light comprising said white light 11 and a second type of light 21 having a relative higher contribution within the wavelength range of 450-500 nm to the total spectral intensity in the visible than the first type of light. The lighting system 1000 may comprise a control unit or controller 50, which may be configured to control one or more lighting units, and especially at least the lighting unit 10. The control unit may e.g. be configured to select a type of light dependent upon the time of the day.

EXPERIMENTAL

Materials and Methods

Participants were tested on the influence of light at different wavelength, with specific attention to wavelengths in the range of 400-540 nm. Comparing different wavelengths showed that alertness increase may occur art different wavelength, but a relative higher increase (relative to other wavelengths) is found in the range of about 400-445 nm, especially 430-445 nm.

Preliminary results also seem to indicate that with this wavelength the response of a human to this light may be controlled in the sense that not only alertness may be controlled but also melatonin production and other biological effects may be controlled. It seems that biological effects of the light at 400-445 may be surprisingly be lower than at higher wavelengths while at the same time a good CRI may be obtained (see below).

Hence, best results in terms of prevention or reduction of melatonin suppression and increasing (or maintaining alertness) is use of light having a wavelength around 437 nm, such as in the range of 430-445 nm. Further, the preliminary results seem to support that the relative reduction of light in the 445-490 nm wavelength range may further contribute to the positive results.

Lighting Units

FIGS. 3a-3d depict spectral distributions of light of number of possible embodiments of the lighting unit. The x-axis indicates the wavelength (in nanometers); the y-axis indicates emission intensity in arbitrary units.

Figure 3A:
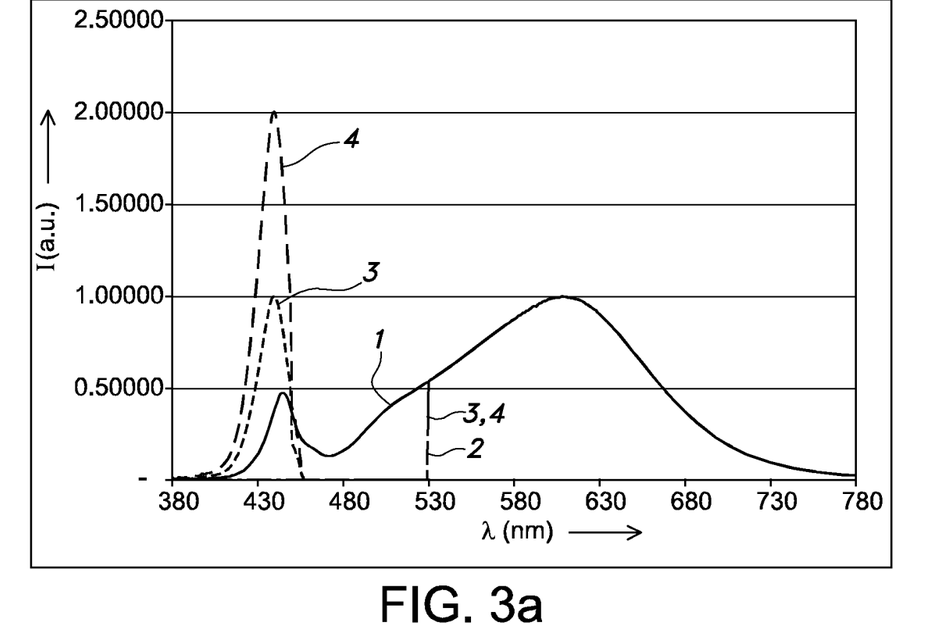
FIGS. 3a-3d show some spectra of light distributions of light of embodiments of the lighting unit.
Figure 3B:
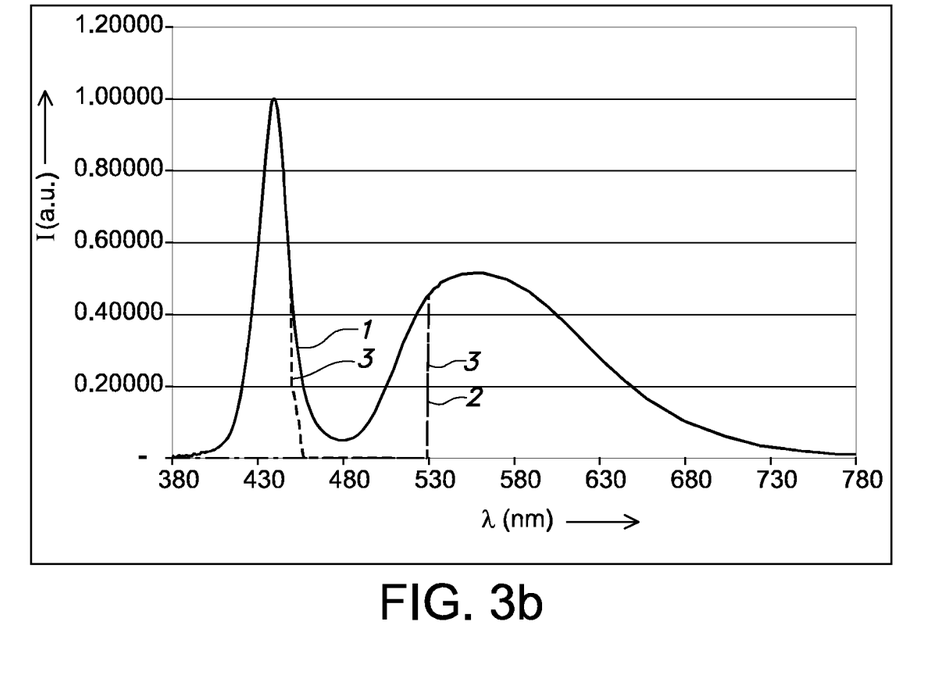

FIGS. 3a and 3b schematically depict lighting units based on a LED light sources with luminescent material such as cerium containing garnet (YAG:Ce and similar garnet compounds), with in the embodiment of FIG. 3a starting with a light source that has a Tc (color temperature), CRT, and R14 as indicated with row 1 in the below table. Row 1 corresponds to the curve indicated with number 1. The curve 2 indicates the result on the spectral light distribution of the light source when applying a cut-off filter; the corresponding values for Tc, CRT and R14 are indicated in the table below. Curve 3 indicates the result on the spectral light distribution of the light source when adding a light source generating violet light around 435 nm; the corresponding values for Tc, CRT and R14 are indicated in the table below. Curve 4 is the same as curve three, but now the intensity of the violet light is doubled relative to curve 3; the corresponding values for Tc, CRT and R14 are also indicated in the table below:

| FIG. 3a | Tc (K) | CRI | R14 |
|---|---|---|---|
| 1 | 2950 | 83 | 78 |
| 2 cut-off | 2300 | 52 | 37 |
| 3 = 2 + Violet | 2400 | 62 | 50 |
| 4 = 2 + 2 * violet | 2700 | 67 | 57 |

FIG. 3b shows a similar setup. However, the starting light source has a higher color temperature (5200 K in FIG. 3b vs. 2950 K in FIG. 3a). The values are provided in the table below:

| FIG. 3b | Tc (K) | CRI | R14 |
|---|---|---|---|
| 1 | 5200 | 66 | 55 |
| 2 cut-off | 3050 | 28 | 9 |
| 3 = 2 + Violet | 4100 | 53 | 37 |

Figure 3C:
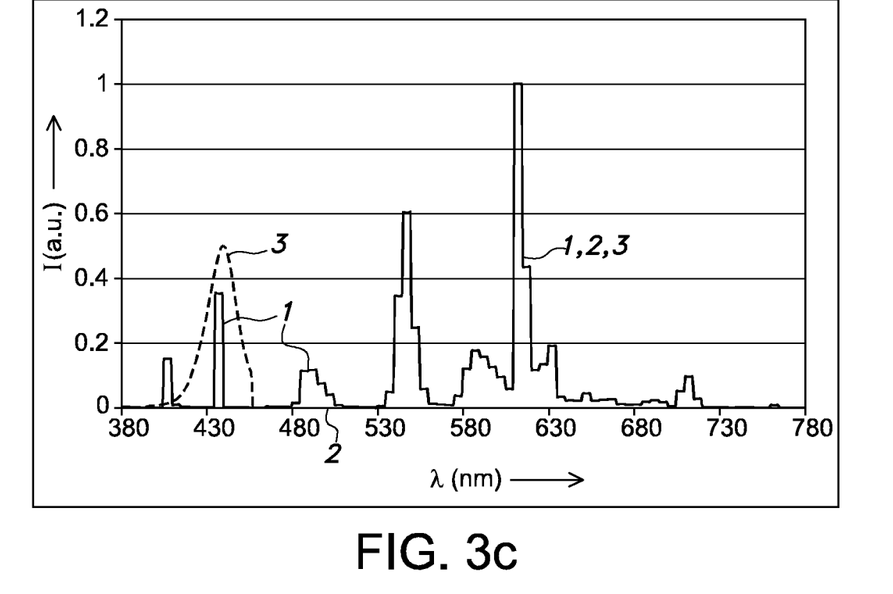
Figure 3D:
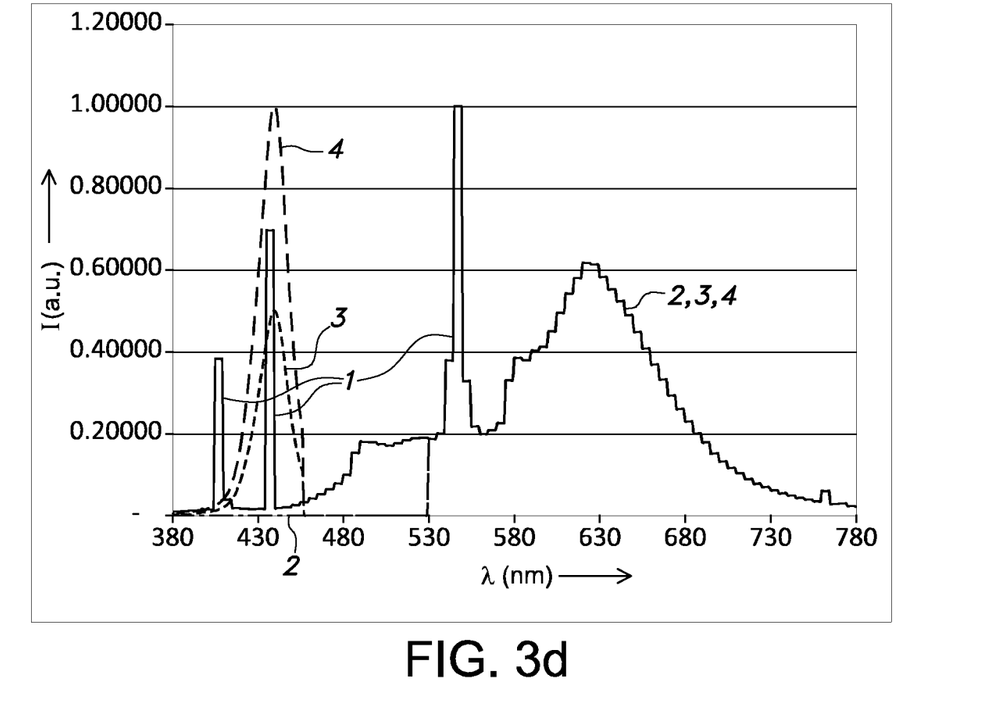

FIGS. 3c and 3d show embodiments wherein the light source comprises a fluorescent lamp, with FIG. 3c showing a fluorescent tri-band lamp and in FIG. 3d the light source comprises a broad band luminescent material (such as halo phosphate).

Row 1 corresponds again to the curve indicated with number 1. The curve 2 indicates the result on the spectral light distribution of the light source when applying a cut-off filter; the corresponding values for Tc, CRT and R14 are indicated in the table below. Curve 3 indicates the result on the spectral light distribution of the light source when adding a light source generating violet light around 435 nm; the corresponding values for Tc, CRT and R14 are indicated in the table below:

| FIG. 3c | Tc (K) | CRI | R14 |
|---|---|---|---|
| 1 | 2600 | 85 | 74 |
| 2 cut-off | 2300 | 65 | 49 |
| 3 = 2 + Violet | 3000 | 79 | 69 |

In FIG. 3d a similar setup is used. However, the starting light source has a slightly higher color temperature (2750 K in FIG. 3d vs. 2600 K in FIG. 3c). The values are provided in the table below. Curve 4 is the same as curve three, but now the intensity of the violet light is doubled relative to curve 3; the corresponding values for Tc, CRT and R14 are also indicated in the table below:

| FIG. 3d | Tc (K) | CRI | R14 |
|---|---|---|---|
| 1 | 2750 | 93 | 91 |
| 2 cut-off | 2300 | 65 | 54 |
| 3 = 2 + Violet | 2300 | 77 | 69 |
| 4 = 2 + 2 * violet | 2550 | 81 | 75 |

In these figures (and tables), the addition of the violet light may be due to a first light source (or first light sources); the other light may be from the second light source (or second light sources). Amongst others based on the above examples, the distribution of photons and other characteristics were evaluated. The results thereof are indicated in the tables below:

| photon number | Reference 1 | Reference 1 + 2 * Violet | Reference 2 | Reference 2 + violet | Violet (per se) |
|---|---|---|---|---|---|
| 430-445 of (380-740) | 3% | 14% | 5% | 15% | 55% |
| 430-445 of 400-500 | 32% | 55% | 39% | 55% | 55% |
| 445-490 of 400-500 | 31% | 24% | 25% | 24% | 24% |
| (430-445)/(445-490) | 104% | 234% | 154% | 228% | 228% |
| mlux/lux | 2.48 | 2.53 | 2.06 | 2.96 | 118 |

| photon number | Reference 3 | Reference 3 + Violet | Reference 3 + 2 * Violet | Reference 4 | Reference 4 + Violet |
|---|---|---|---|---|---|
| 430-445 of (380-740) | 2% | 6% | 12% | 11% | 13% |
| 430-445 of 400-500 | 24% | 61% | 61% | 47% | 61% |
| 445-490 of 400-500 | 53% | 16% | 16% | 31% | 16% |
| (430-445)/(445-490) | 46% | 385% | 385% | 155% | 385% |
| mlux/lux | 2.52 | 1.44 | 2.17 | 3.53 | 2.22 |

The references indicate normal spectral distributions and violet refers to a specific violet light source. The other examples in the table refer to those references spectra that are depleted in blue-green and have a violet light source (sometimes also with two times the violet intensity, by way of example). The data related to reference 1 refer to FIG. 3d and the data related to reference 2 refer to FIG. 3c; the data related to reference 3 relate to FIG. 3a and the data related to reference 4 relate to FIG. 3b.

Hence, in general the white light (11) has a ratio of the total number of photons in the wavelength range of 445-490 nm to the total number of photons wavelength range of 430-445 nm of at maximum 0.75, especially at maximum 0.5, often even at maximum 0.3.

Therefore, with the present lighting units a sufficient or even good CRI may be obtained while on the same time relatively increasing alertness and controlling biological impact (on a vertebrate). Especially, the lighting unit can be used for providing light 11 with a CRI (color rendering index) above 60, and controlling a biological response of a human on said light 11.

The invention claimed is:

1. A lighting unit comprising at least one solid state light source, the lighting unit configured to generate white light wherein the white light has a spectral intensity in the visible spectrum wherein at least 40% of all photons in the wavelength range of 400-500 nm are found in the wavelength range of 430-445 nm, form an intensity peak at 437 nm, and are generated, at least in part, by the at least one solid state light source, and wherein the white light has a ratio of the total number of photons in the wavelength range of 445-490 nm to the total number of photons in the wavelength range of 430-445 nm of at maximum 0.75.

2. The lighting unit according to claim 1, wherein at least 50% of all photons in the wavelength range of 400-500 nm are found in the wavelength range of 430-445 nm, wherein the white light has a ratio of the total number of photons in the wavelength range of 445-490 nm to the total number of photons in the wavelength range of 430-445 nm of at maximum 0.5.

3. The lighting unit according to claim 1, comprising:
   a first light source, included in said at least one solid state light source, configured to generate first light source light having spectral intensity in the visible spectrum, wherein at least 50% of the photons in the visible spectrum of the first light source light are found in the wavelength range of 430-445 nm, and
   a second light source, distinct from said at least one solid state light source, configured to generate second light source light having spectral intensity in the visible spectrum, wherein at least 50% of all photons in the visible spectrum of the second light source light are found in the range of at least 500 nm, and
wherein the first light source and the second light source are configured to generate said white light.

4. The lighting unit according to claim 3, wherein the second light source comprises a second solid state light source and a luminescent material configured to convert second solid state light source light into luminescent material light, wherein the second solid state light source with the luminescent material is configured to provide said second light source light.

5. The lighting unit according to claim 3, wherein the second light source comprises a fluorescent lamp.

6. The lighting unit according to claim 3, wherein at least one of the first light source or the second light source includes an optical filter comprising a luminescent material.

7. The lighting unit according to claim 1, comprising an optical filter configured to reduce propagation of light having a wavelength in the range of 450-500 nm.

8. The lighting unit according to claim 1, comprising:
   a first solid state light source, included in said at least one solid state light source, configured to generate first solid state light source light having spectral intensity in the visible spectrum, wherein at least 50% of the photons in the visible spectrum of the first solid state light source light are found in the wavelength range of 430-445 nm;
   a second solid state light source, distinct from said at least one solid state light source, configured to generate second solid state light source light having spectral intensity in the visible spectrum, wherein at least 50% of the photons in the visible spectrum of the second solid state light source light are found in the wavelength range of 500-570 nm; and
   a third solid state light source, distinct from said at least one solid state light source, configured to generate third solid state light source light having spectral intensity in the visible spectrum, wherein at least 50% of the photons in the visible spectrum of the third solid state light source light are found in the wavelength range of 600-750 nm,
wherein the first solid state light source, the second solid state light source and the third solid state light source are configured to generate said white light.

9. The lighting unit according to claim 1, having an optical power (Watt) in the wavelength range of 445-490 nm which is less than 20% of the total optical power in the visible spectrum.

10. The lighting unit according to claim 1, wherein the white light has a Color Rendering Index (CRI) of at least 60.

11. A lighting system comprising the lighting unit according to claim 1 and a further lighting unit, wherein the lighting system is configured to provide at the same time or at different times at least two types of light, with a first type of light comprising said white light and a second type of light having a higher contribution within the wavelength range of 450-500 nm to the total spectral intensity in the visible spectrum than the first type of light.

12. The lighting unit according to claim 1, wherein the at least one solid state light source is configured to produce at least a majority of said at least 40% of all photons in the wavelength range of 400-500 nm that are found in the wavelength range of 430-445 nm.

13. The lighting unit according to claim 12, wherein said intensity peak has an intensity that is at least half of an intensity of a highest intensity peak in said white light.

14. The lighting unit according to claim 1, wherein the at least one solid state light source is configured to produce a totality of said at least 40% of all photons in the wavelength range of 400-500 nm that are found in the wavelength range of 430-445 nm.

15. The lighting unit according to claim 14, wherein said intensity peak has an intensity that is at least half of an intensity of a highest intensity peak in said white light.

16. The lighting unit according to claim 1, wherein said intensity peak has an intensity that is at least half of an intensity of a highest intensity peak in said white light.

* * * * *